United States Patent
Fomitchev et al.

(10) Patent No.: US 10,407,571 B2
(45) Date of Patent: *Sep. 10, 2019

(54) HYDROPHOBIC-TREATED METAL OXIDE

(71) Applicant: Cabot Corporation, Boston, MA (US)

(72) Inventors: Dmitry Fomitchev, Lexington, MA (US); Joachim K. Floess, Urbana, IL (US); William R. Williams, Charlotte, NC (US); Hairuo Tu, Boxborough, MA (US)

(73) Assignee: Cabot Corporation, Boston, MA (US)

( * ) Notice: Subject to any disclaimer, the term of this patent is extended or adjusted under 35 U.S.C. 154(b) by 296 days.

This patent is subject to a terminal disclaimer.

(21) Appl. No.: 15/454,089

(22) Filed: Mar. 9, 2017

(65) Prior Publication Data

US 2017/0174897 A1 Jun. 22, 2017

Related U.S. Application Data

(62) Division of application No. 11/774,465, filed on Jul. 6, 2007, now abandoned.

(60) Provisional application No. 60/844,828, filed on Sep. 15, 2006.

(51) Int. Cl.
*C09C 1/30* (2006.01)
*C07F 7/18* (2006.01)
*B82Y 30/00* (2011.01)
*C09C 3/12* (2006.01)
*G03G 9/097* (2006.01)
*C07F 7/10* (2006.01)

(52) U.S. Cl.
CPC ............ *C09C 1/3081* (2013.01); *B82Y 30/00* (2013.01); *C07F 7/10* (2013.01); *C07F 7/1804* (2013.01); *C09C 3/12* (2013.01); *G03G 9/09708* (2013.01); *G03G 9/09716* (2013.01); *G03G 9/09725* (2013.01); *C01P 2002/86* (2013.01); *C01P 2004/62* (2013.01); *C01P 2004/64* (2013.01); *C01P 2006/10* (2013.01); *C01P 2006/11* (2013.01); *C01P 2006/12* (2013.01); *Y10T 428/2982* (2015.01)

(58) Field of Classification Search
CPC . C09C 1/3081; C09C 3/12; C07F 7/10; C07F 7/1836; G03G 9/09708; G03G 9/09725; G03G 9/09716; B82Y 30/00; Y10T 428/2982; C01P 2004/62; C01P 2006/10; C01P 2006/12; C01P 2004/64; C01P 2002/86; C01P 2006/11
See application file for complete search history.

(56) References Cited

U.S. PATENT DOCUMENTS

| | | |
|---|---|---|
| 3,900,588 A | 8/1975 | Fisher |
| 4,539,351 A | 9/1985 | O'Malley et al. |
| 4,845,004 A | 7/1989 | Kobayashi |
| 4,923,520 A | 5/1990 | Anzai et al. |
| 4,943,507 A | 7/1990 | Takahashi et al. |
| 4,950,502 A | 8/1990 | Saam et al. |
| 4,985,477 A | 1/1991 | Collins et al. |
| 5,008,305 A | 4/1991 | Kennan et al. |
| 5,009,874 A | 4/1991 | Parmentier et al. |
| 5,013,585 A | 5/1991 | Shimizu et al. |
| 5,024,915 A | 6/1991 | Sato et al. |
| 5,039,736 A | 8/1991 | Fujiki |
| 5,096,733 A | 3/1992 | Vallyathan et al. |
| 5,135,832 A | 8/1992 | Sacripante et al. |
| 5,194,356 A | 3/1993 | Sacripante et al. |
| 5,226,930 A | 7/1993 | Sasaki |
| 5,266,432 A | 11/1993 | Hayashi et al. |
| 5,320,925 A | 6/1994 | Imai et al. |
| 5,376,172 A | 12/1994 | Tripp et al. |
| 5,415,936 A | 5/1995 | Deusser et al. |
| 5,422,214 A | 6/1995 | Akiyama et al. |
| 5,424,161 A | 6/1995 | Hayashi et al. |
| 5,475,044 A | 12/1995 | Stein |
| 5,480,755 A | 1/1996 | Uchiyama et al. |
| 5,484,678 A | 1/1996 | Pickering et al. |
| 5,531,929 A | 7/1996 | Kobayashi |
| 5,543,173 A | 8/1996 | Horn, Jr. et al. |
| 5,597,853 A | 1/1997 | Itoh et al. |
| 5,651,921 A | 7/1997 | Kaijou |
| 5,665,156 A | 9/1997 | Ettlinger et al. |
| 5,665,511 A | 9/1997 | Imai et al. |
| 5,686,054 A | 11/1997 | Barthel et al. |
| 5,711,797 A | 1/1998 | Ettlinger et al. |
| 5,716,748 A | 2/1998 | Hasegawa et al. |
| 5,718,907 A | 2/1998 | Labarre |
| 5,725,987 A | 3/1998 | Combes et al. |
| 5,747,211 A | 5/1998 | Hagi et al. |
| 5,766,814 A | 6/1998 | Baba et al. |
| 5,776,240 A | 7/1998 | Deller et al. |
| 5,776,646 A | 7/1998 | Hagi et al. |

(Continued)

FOREIGN PATENT DOCUMENTS

| | | |
|---|---|---|
| CN | 1688509 A | 10/2005 |
| DE | 19616781 A1 | 11/1997 |

(Continued)

OTHER PUBLICATIONS

Maciel, et al., "Silicon-29 NMR Study of the Surface of Silica Gel by Cross Polarization and Magic-Angle Spinning", J. Am. Chem. Soc., 102 (25), pp. 7606-7607 (Dec. 3, 1980).

Sindorf, et al., "Cross-Polarization/Magic-Angle Spinning Silicon-29 Nuclear Magnetic Resonance Study of Silica Gel Using Trimethylsilane Bonding as a Probe of Surface Geometry and Reactivity", J. Phys. Chem., 86 (26), pp. 5208-5219 (Dec. 23, 1982).

Sindorf, et al., "Solid-State NMR Studies of the Reactions of Silica Surfaces with Polyfunctional Chloromethylsilanes and Ethoxymethylsilanes", J. Am. Chem. Soc., 105 (12), pp. 3767-3776 (Jun. 15, 1983).

(Continued)

Primary Examiner — Richard M Rump

(57) ABSTRACT

This invention provides metal oxide particles surface-treated with a hydrophobicity-imparting agent, methods of making such, and toner compositions comprising the same.

16 Claims, No Drawings

(56) References Cited

U.S. PATENT DOCUMENTS

| | | |
|---|---|---|
| 5,824,442 A | 10/1998 | Tanikawa et al. |
| 5,824,739 A | 10/1998 | Kondo et al. |
| 5,827,632 A | 10/1998 | Inaba et al. |
| 5,840,287 A | 11/1998 | Guskey et al. |
| 5,843,525 A | 12/1998 | Shibasaki et al. |
| 5,849,451 A | 12/1998 | Ishihara et al. |
| 5,900,315 A | 5/1999 | Little |
| 5,902,635 A | 5/1999 | Garafalo et al. |
| 5,908,660 A | 6/1999 | Griffith et al. |
| 5,916,722 A | 6/1999 | Creatura et al. |
| 5,919,298 A | 7/1999 | Griffith et al. |
| 5,942,590 A | 8/1999 | Burns et al. |
| 5,959,005 A | 9/1999 | Hartmann et al. |
| 5,969,023 A | 10/1999 | Enami et al. |
| 5,989,768 A | 11/1999 | Little |
| 6,004,711 A | 12/1999 | Bourne et al. |
| 6,004,714 A | 12/1999 | Ciccarelli et al. |
| 6,015,843 A | 1/2000 | Van Vlasselaer et al. |
| 6,025,455 A | 2/2000 | Yoshitake et al. |
| 6,045,650 A | 4/2000 | Mitchnick et al. |
| 6,051,672 A | 4/2000 | Burns et al. |
| 6,066,421 A | 5/2000 | Julien et al. |
| 6,077,640 A | 6/2000 | Komai et al. |
| 6,086,668 A | 7/2000 | Farneth et al. |
| 6,087,059 A | 7/2000 | Duggan et al. |
| 6,103,441 A | 8/2000 | Tomita et al. |
| 6,107,351 A | 8/2000 | Burns et al. |
| 6,165,663 A | 12/2000 | Baba et al. |
| 6,174,926 B1 | 1/2001 | Menon et al. |
| 6,180,076 B1 | 1/2001 | Uhrlandt et al. |
| 6,183,867 B1 | 2/2001 | Barthel et al. |
| 6,184,408 B1 | 2/2001 | Burns et al. |
| 6,190,815 B1 | 2/2001 | Ciccarelli et al. |
| 6,191,122 B1 | 2/2001 | Lux et al. |
| 6,193,795 B1 | 2/2001 | Nargiello et al. |
| 6,197,384 B1 | 3/2001 | Schubert et al. |
| 6,197,470 B1 | 3/2001 | Tamura |
| 6,203,960 B1 | 3/2001 | Ciccarelli et al. |
| 6,214,507 B1 | 4/2001 | Sokol et al. |
| 6,242,147 B1 | 6/2001 | Anno et al. |
| 6,248,495 B1 | 6/2001 | Inokuchi et al. |
| 6,255,373 B1 | 7/2001 | Akamatsu et al. |
| 6,270,937 B2 | 8/2001 | Yuasa et al. |
| 6,287,739 B1 | 9/2001 | Kawakami et al. |
| 6,294,303 B1 | 9/2001 | Putnam et al. |
| 6,312,861 B1 | 11/2001 | Ciccarelli et al. |
| 6,316,155 B1 | 11/2001 | Kudo et al. |
| 6,318,124 B1 | 11/2001 | Rutherford et al. |
| 6,319,647 B1 | 11/2001 | Gutman et al. |
| 6,335,139 B1 | 1/2002 | Gambayashi et al. |
| 6,374,637 B1 | 4/2002 | Costa et al. |
| 6,376,077 B1 | 4/2002 | Hiraishi et al. |
| 6,379,856 B2 | 4/2002 | Sokol et al. |
| 6,384,125 B1 | 5/2002 | Bergstrom et al. |
| 6,403,271 B1 | 6/2002 | Suzuki et al. |
| 6,420,456 B1 | 7/2002 | Koski |
| 6,448,331 B1 | 9/2002 | Ioka et al. |
| 6,465,670 B2 | 10/2002 | Thise et al. |
| 6,479,206 B1 | 11/2002 | Suzuki et al. |
| 6,489,075 B2 | 12/2002 | Suzuki et al. |
| 6,503,677 B1 | 1/2003 | Gutman et al. |
| 6,521,290 B1 | 2/2003 | Kudo et al. |
| 6,555,282 B2 | 4/2003 | Okuno et al. |
| 6,573,018 B2 | 6/2003 | Ishibashi et al. |
| 6,579,929 B1 | 6/2003 | Cole et al. |
| 6,589,703 B2 | 7/2003 | Steller et al. |
| 6,610,777 B1 | 8/2003 | Anderson et al. |
| 6,613,491 B2 | 9/2003 | Inoue et al. |
| 6,657,001 B1 | 12/2003 | Anderson et al. |
| 6,677,095 B2 | 1/2004 | Murota et al. |
| 6,686,110 B2 | 2/2004 | Kadota |
| 6,696,212 B2 | 2/2004 | Marsh et al. |
| 6,706,398 B1 | 3/2004 | Revis |
| 6,706,457 B2 | 3/2004 | Koumura |
| 6,736,891 B1 | 5/2004 | Bice et al. |
| 6,780,559 B2 | 8/2004 | Veregin et al. |
| 6,800,413 B2 | 10/2004 | Barthel et al. |
| 6,803,408 B2 | 10/2004 | Anderson et al. |
| 6,811,856 B2 | 11/2004 | Nun et al. |
| 6,830,811 B2 | 12/2004 | Chao |
| 6,840,992 B2 | 1/2005 | Glaum et al. |
| 6,855,759 B2 | 2/2005 | Kudo et al. |
| 6,890,657 B2 | 5/2005 | Pickering et al. |
| 6,899,948 B2 | 5/2005 | Zhang et al. |
| 6,899,951 B2 | 5/2005 | Panz et al. |
| 6,972,301 B2 | 12/2005 | Hurlburt et al. |
| 7,014,969 B2 | 3/2006 | Yachi et al. |
| 7,014,975 B2 | 3/2006 | Barthel et al. |
| 7,022,375 B2 | 4/2006 | Schachtely et al. |
| 7,081,234 B1 | 7/2006 | Qi et al. |
| 7,083,770 B2 | 8/2006 | Shibasaki et al. |
| 7,169,832 B2 | 1/2007 | Poppe et al. |
| 7,186,440 B2 | 3/2007 | Yoshitake et al. |
| 7,214,459 B2 | 5/2007 | Iizuka et al. |
| 7,238,387 B2 | 7/2007 | Ogawa et al. |
| 7,252,885 B2 | 8/2007 | Pickering et al. |
| 7,262,233 B2 | 8/2007 | Isarov et al. |
| 7,300,734 B2 | 11/2007 | McDougall et al. |
| 7,312,009 B2 | 12/2007 | Lee et al. |
| 7,316,881 B2 | 1/2008 | Rimai et al. |
| 7,341,625 B2 | 3/2008 | Amirzadeh-Asi |
| 7,422,834 B2 | 9/2008 | Akiyama et al. |
| 7,713,326 B2 | 5/2010 | Carstens et al. |
| 7,713,626 B2 | 5/2010 | Meyer et al. |
| 7,799,870 B2 | 9/2010 | Hergenrother et al. |
| 2002/0037936 A1 | 3/2002 | Michael et al. |
| 2003/0035888 A1 | 2/2003 | Eriyama et al. |
| 2003/0082090 A1 | 5/2003 | Blume et al. |
| 2004/0077768 A1 | 4/2004 | Greenwood |
| 2004/0102529 A1 | 5/2004 | Campbell et al. |
| 2004/0138343 A1 | 7/2004 | Campbell et al. |
| 2005/0011409 A1 | 1/2005 | Isobe |
| 2005/0014894 A1 | 1/2005 | Flannigan et al. |
| 2005/0026060 A1 | 2/2005 | Ogawa et al. |
| 2005/0026087 A1 | 2/2005 | Keller |
| 2005/0026089 A1 | 2/2005 | Ogawa et al. |
| 2005/0089353 A1 | 4/2005 | Pickering et al. |
| 2005/0095521 A1 | 5/2005 | Rimai et al. |
| 2005/0095522 A1 | 5/2005 | Goebel et al. |
| 2005/0113488 A1 | 5/2005 | Isarov et al. |
| 2005/0147908 A1 | 7/2005 | Yamane et al. |
| 2005/0154124 A1 | 7/2005 | Yoshitake et al. |
| 2005/0164109 A1 | 7/2005 | Iizuka et al. |
| 2005/0170109 A1 | 8/2005 | Chen et al. |
| 2005/0187334 A1 | 8/2005 | Blume et al. |
| 2005/0192395 A1 | 9/2005 | Panz |
| 2005/0203214 A1 | 9/2005 | Amano et al. |
| 2005/0241531 A1 | 11/2005 | Meyer et al. |
| 2006/0041035 A1 | 2/2006 | Poppe et al. |
| 2006/0046178 A1 | 3/2006 | Akiyama et al. |
| 2006/0062941 A1 | 3/2006 | Bi et al. |
| 2006/0084746 A1 | 4/2006 | Bice et al. |
| 2006/0099129 A1 | 5/2006 | Stenzel et al. |
| 2006/0112860 A1 | 6/2006 | Yoshitake et al. |
| 2006/115405 A1 | 6/2006 | Konya et al. |
| 2006/0121381 A1 | 6/2006 | McDougall et al. |
| 2006/0121382 A1 | 6/2006 | Choi et al. |
| 2006/0127787 A1 | 6/2006 | Lee et al. |
| 2006/0150527 A1 | 7/2006 | Ohara et al. |
| 2006/0160008 A1 | 7/2006 | Lee et al. |
| 2006/0171872 A1 | 8/2006 | Adams |
| 2006/0178451 A1 | 8/2006 | Weller |
| 2006/0188722 A1 | 8/2006 | White et al. |
| 2006/0217473 A1 | 9/2006 | Hergenrother et al. |
| 2006/0225615 A1 | 10/2006 | Raman et al. |
| 2006/0281009 A1 | 12/2006 | Boyer et al. |
| 2007/0009823 A1 | 1/2007 | Skorokhod et al. |
| 2007/0048643 A1 | 3/2007 | Kmiecik-Lawrynowicz et al. |
| 2007/0148577 A1 | 6/2007 | Ogawa et al. |
| 2007/0191537 A1 | 8/2007 | Meyer et al. |
| 2008/0069753 A1 | 3/2008 | Floess et al. |
| 2008/0070140 A1 | 3/2008 | Fomitchev et al. |

(56) References Cited

U.S. PATENT DOCUMENTS

| | | |
|---|---|---|
| 2008/0070143 A1 | 3/2008 | Fomitchev et al. |
| 2013/0129597 A1 | 5/2013 | Fomitchev et al. |

FOREIGN PATENT DOCUMENTS

| | | |
|---|---|---|
| EP | 0371147 B1 | 6/1990 |
| EP | 0694576 A1 | 1/1996 |
| EP | 0704769 A1 | 5/1996 |
| EP | 0982268 A1 | 3/2000 |
| EP | 1559750 A2 | 8/2005 |
| EP | 1580019 A1 | 9/2005 |
| EP | 1559750 A3 | 10/2005 |
| EP | 1591490 A2 | 11/2005 |
| EP | 1657283 A1 | 5/2006 |
| EP | 1696006 A1 | 8/2006 |
| JP | 58-216252 A | 12/1983 |
| JP | 62-227160 A | 10/1987 |
| JP | 02-017932 A | 1/1990 |
| JP | 03-187913 A | 8/1991 |
| JP | 04-106184 A | 4/1992 |
| JP | 04-269763 A | 9/1992 |
| JP | 05-257316 A | 10/1993 |
| JP | 05-279041 A | 10/1993 |
| JP | 06-100313 A | 4/1994 |
| JP | 06-194863 A | 7/1994 |
| JP | 06-242630 A | 9/1994 |
| JP | 07-064318 A | 3/1995 |
| JP | 07-187647 A | 7/1995 |
| JP | 08-095285 A | 4/1996 |
| JP | 08-119619 A | 5/1996 |
| JP | 08-245835 A | 9/1996 |
| JP | 10-025427 A | 1/1998 |
| JP | 10-036705 A | 2/1998 |
| JP | 10-087317 A | 4/1998 |
| JP | 11-246210 A | 9/1999 |
| JP | 2000-044226 A | 2/2000 |
| JP | 2000-258955 A | 9/2000 |
| JP | 2001-031843 A | 2/2001 |
| JP | 2001-097710 A | 4/2001 |
| JP | 2001-305804 A | 11/2001 |
| JP | 2002-029730 A | 1/2002 |
| JP | 2002-146233 A | 5/2002 |
| JP | 2002-244340 A | 8/2002 |
| JP | 2002-256170 A | 9/2002 |
| JP | 2002-275356 A | 9/2002 |
| JP | 2002-338230 A | 11/2002 |
| JP | 2003-137528 A | 5/2003 |
| JP | 2003-171117 A | 6/2003 |
| JP | 2003-201112 A | 7/2003 |
| JP | 2003-238141 A | 8/2003 |
| JP | 2004-029699 A | 1/2004 |
| JP | 2004-101887 A | 4/2004 |
| JP | 2004-168559 A | 6/2004 |
| JP | 2004-258265 A | 9/2004 |
| JP | 2004-359476 A | 12/2004 |
| JP | 2005-003726 A | 1/2005 |
| JP | 2005-015251 A | 1/2005 |
| JP | 2005-215491 A | 8/2005 |
| JP | 2005-536611 A | 12/2005 |
| JP | 2006-022316 A | 1/2006 |
| JP | 2006-053458 A | 2/2006 |
| JP | 2006-096641 A | 4/2006 |
| JP | 2006-169096 A | 6/2006 |
| JP | 2006-171017 A | 6/2006 |
| JP | 2007-034223 A | 2/2007 |
| JP | 2007-034224 A | 2/2007 |
| JP | 2007-526374 A | 9/2007 |
| JP | 2008-516889 A | 5/2008 |
| WO | WO 2004/031076 A1 | 4/2004 |
| WO | WO 2004/035473 | 4/2004 |
| WO | WO 2005/095525 A1 | 10/2005 |
| WO | WO 2006/045012 A2 | 4/2006 |
| WO | WO 2006/053632 A2 | 5/2006 |
| WO | WO 2006/056377 A1 | 6/2006 |
| WO | WO 2006/116887 A1 | 11/2006 |
| WO | WO 2007/013388 A1 | 2/2007 |

OTHER PUBLICATIONS

Yoshida, "Silica Nucleation, Polymerization, and Growth Preparation of Monodispersed Sols", in Coloidal Silica, Fundamentals and Applications (Bergna, et al., eds.), Chapter 6, pp. 47-56 (CRC Press, an imprint of the Taylor & Francis Group, Boca Raton, Florida, 2006).

Chen, et al., Journal of Colloid and Interface Science, 281, pp. 339-350 (2005).

Evonik Industries, Aerosil Product Overview (Evonik Degussa GmbH, 2009).

International Search Report in International Patent Application No. PCT/US2007/020007 (dated Mar. 6, 2008).

International Search Report in International Patent Application No. PCT/US2008/008287 (dated Oct. 21, 2008).

International Search Report in International Patent Application No. PCT/US2008/008292 (dated Nov. 14, 2008).

International Search Report in International Patent Application No. PCT/US2008/008293 (dated Oct. 21, 2008).

International Preliminary Report on Patentability in International Patent Application No. PCT/US2007/020007 (dated Mar. 17, 2009).

International Preliminary Report on Patentability in International Patent Application No. PCT/US2008/008287 (dated Jan. 21, 2010).

International Preliminary Report on Patentability in International Patent Application No. PCT/US2008/008292 (dated Jan. 21, 2010).

International Preliminary Report on Patentability in International Patent Application No. PCT/US2008/008293 (dated Jan. 21, 2010).

Caravajal, et al., "Structural Characterization of (3-Aminophropyl) triethoxysilane-Modified Silicas by Silicon-29 and Carbon-13 Nuclear Magnetic Resonance", Analytical Chemistry, 60(17), pp. 1776-1786 (Sep. 1, 1988).

Garcia, et al., "Use of p-Toluenesulfonic Acid for the Controlled Grafting of Alkoxysilanes onto Silanol Containing Surfaces: Preparation of Tunable Hydrophilic, Hydrophobic, and Super-Hydrophobic Silica", J. Am. Chem. Soc., 129, pp. 5052-5060 (2007).

Cabot Corporation, CAB-O-SIL TS-530 Treated Fumed Silica (Cabot Corporation, Sep. 2008).

Cabot Corporation, CAB-O-SIL TS-720 Treated fumed Silica (Cabot Corporation, Sep. 2008).

Degussa, Aerosil R. 972 Hydrophobic Fumed Silica Product Information (Degussa AG, May 2005).

Evonik Industries, Aerosil R. 972 Pharma Hydrophobic Colloidal Anhydrous Silica (Evonik Degussa GmbH, Feb. 2007).

Iler, "Colloidal Silica," in The Colloid Chemistry of Silica and Silicates, Chapter V, pp. 87-98 (Cornell University Press, London, 1955).

Zumdahl, "Colloids", in Chemistry, $5^{th}$ Edition (Stratton et al., eds), Chapter 11.8, pp. 548-550 (Houghton Mifflin Company, Boston, MA, 2000).

Julien, et al., "My Toner Technology", in Handbook of Imaging Materials, $2^{nd}$ Edition (Diamond et al., eds.), Chapter 5, pp. 173-204 (Marcel Dekker, Inc., New York, 2002).

Patent Office of the People's Republic of China, Office Action in Chinese Patent Application No. 200780034354.6 (dated Nov. 30, 2011).

Patent Office of the People's Republic of China, Office Action in Chinese Patent Application No. 200880105851.5 (dated May 3, 2012).

Gomis, et al., "LLE, VLE and VLLE data for the water-n-butanol-n-hexane system at atmospheric pressure", Fluid Phase Equilibria, 316, pp. 135-140 (2012).

Ochiai, Mitsuru, "Finely Dispersed Anhydrous Silica", in Illustrated Powder Properties, $3^{rd}$ edition, Jyun-ichiro Tsubaki (editor), NGT Corporation, Tachikawa, Tokyo, Japan (publisher), p. 549 (Jun. 30, 2004).

(56) References Cited

OTHER PUBLICATIONS

Nissan Chemical Industries, Ltd., "Snowtex-O", Information Leaflet (2006) [as printed from http://db.nissanchem.co.jp/db/details.php?id=111 on Nov. 1, 2011]. (Partial English Translation).

Japanese Patent Office; Office Action in Japanese Patent Application No. 2009-528305 (dated Oct. 16, 2012). (English Translation).

Nissan Chemical Industries, Ltd., "Snowtex-O", Information Leaflet (2006) [as printed from http://db.nissanchem.co.jp/db/details.php?id=111 on Jun. 5, 2013]. (See JPO Office action in Japanese Patent Application No. 2010-514878 (Jun. 11, 2013).

Japanese Patent Office; Office Action in Japanese Patent Application No. 2010-514878 (dated Jun. 11, 2013). (English Translation).

Japanese Patent Office; Office Action in Japanese Patent Application No. 2010-514881 (dated Mar. 25, 2014). (English Translation).

Japanese Patent Office; Office Action in Japanese Patent Application No. 2010-514878 (dated Jul. 29, 2014). (English Translation).

Korean Patent Office; Office Action in Korean Patent Application No. 10-2010-7000107 (dated Aug. 21, 2014). (English Translation).

Korean Patent Office; Office Action in Korean Patent Application No. 10-2010-7000108 (dated Aug. 21, 2014). (English Translation).

Korean Patent Office; Office Action in Korean Patent Application No. 10-2010-7000105 (dated Aug. 26, 2014). (English Translation).

Krysztafkiewicz, et al., "Precipitated Silicas Modified with 3-aminopropyltriethoxysilane", Colloids and Surfaces, A: Physiocochemical and Engineering Aspects, 173, pp. 73-84 (2000).

Japanese Patent Office; Office Action in Japanese Patent Application No. 2010-514881 (dated Oct. 21, 2014). (English Translation).

Korean Patent Office; Office Action in Korean Patent Application No. 10-2014-7030104 (dated Dec. 17, 2014). (English Translation).

Gellermann, et al., "Synthesis and Characterization of the Organic Surface Modificiations of Monodisperse Colloidal Silica", Journal of Sol-Gel Science and Technology, 8, pp. 173-176 (1997).

Japanese Patent Office; Office Action in Japanese Patent Application No. 2014-226820 (dated Sep. 15, 2015). English Translation.

HYDROPHOBIC-TREATED METAL OXIDE

CROSS-REFERENCE TO RELATED APPLICATIONS

This patent application is a divisional application of U.S. patent application Ser. No. 11/774,465, filed Jul. 6, 2007, which claims the benefit of U.S. Provisional Patent Application No. 60/844,828, filed Sep. 15, 2006, which is incorporated by reference.

BACKGROUND OF THE INVENTION

Hydrophobic metal oxide particles possess physical properties that are useful in a number of applications requiring a high degree of dispersibility. Some hydrophobic metal oxide particles have physical properties that are desirable for use in toner compositions.

Untreated metal oxide particles are hydrophilic due to the presence of polar groups, such as hydroxyl groups (—OH), on the surface of the untreated silica particles. By treating hydrophilic metal oxide particles, the hydrophilic nature of the particles can be reduced, thereby imparting varying degrees of hydrophobicity to the particles.

Many different methods are known for treating the surface of metal oxide particles. However, the direct treatment of an aqueous dispersion of metal oxide particles is often inefficient or difficult to achieve. Thus, there remains a desire for additional treated metal oxide particles, especially those that are useful for modifying the charge of toner particles, and for additional methods of preparing such hydrophobic metal oxide particles, especially methods that can be used to prepare hydrophobic metal oxide particles directly from an aqueous dispersion of the metal oxide particles.

BRIEF SUMMARY OF THE INVENTION

The invention provides a particle composition comprising metal oxide particles surface-treated with a first hydrophobicity-imparting agent and, optionally, a second hydrophobicity-imparting agent, which metal oxide particles are hydrophobic, non-aggregated, and contain substantially no free alkali metal cations.

The invention also provides a toner composition comprising toner particles and metal oxide particles surface-treated with a first hydrophobicity-imparting agent and, optionally, a second hydrophobicity-imparting agent, which metal oxide particles are hydrophobic and contain substantially no free alkali metal cations.

The invention further provides a method of preparing hydrophobic metal oxide particles comprising (a) providing an aqueous dispersion of metal oxide particles, wherein the aqueous dispersion is acidic or basic, (b) combining the dispersion with a first hydrophobicity-imparting agent and, optionally, a second hydrophobicity-imparting agent to provide a reaction mixture, and (c) drying the reaction mixture to provide hydrophobic metal oxide particles, wherein the hydrophobic metal oxide particles contain substantially no free alkali metal cations.

DETAILED DESCRIPTION OF THE INVENTION

The invention provides a particle composition comprising metal oxide particles surface-treated with a first hydrophobicity-imparting agent, which metal oxide particles are hydrophobic, non-aggregated, and contain substantially no free alkali metal cations.

The metal oxide particles can comprise any suitable type of metal oxide. For example, the metal oxide particles can comprise silica, alumina, ceria, or titania. Preferably, the metal oxide particles are colloidal metal oxide particles, such as colloidal silica particles. Colloidal metal oxide particles are non-aggregated, individually discrete particles, which typically are spherical or nearly spherical in shape, but can have other shapes (e.g., shapes with generally elliptical, square, or rectangular cross-sections). Such particles are structurally different from fumed or pyrogenically prepared particles, which are chain-like structures of aggregated primary particles.

Non-aggregated metal oxides (e.g., colloidal metal oxides), which can be treated to provide a treated metal oxide in accordance with the invention, are commercially available, or can be prepared by known methods from various starting materials (e.g., wet-process type metal oxides). Typically, the colloidal metal oxide starting material will be available as a sol, which is a dispersion of colloidal metal oxide in a suitable solvent, most often water alone or with a co-solvent and/or stabilizing agent. See, e.g., Akitoshi Yoshida, *Silica Nucleation, Polymerization, and Growth Preparation of Monodispersed Sols*, in Colloidal Silica Fundamentals and Applications 47-56 (H. E. Bergna & W. O. Roberts, eds., 2006). Non-limiting examples of commercially available colloidal silica products suitable for use in the invention include SNOWTEX® products from Nissan Chemical, NexSil™ and NexSil A™ series products available from Nyacol Nanotechnologies, Inc., and Levasil® products available from H.C.Starck.

The non-aggregated metal oxide particles from which the treated metal oxide particles are prepared often will comprise alkali metal cations as a result of the method by which the non-aggregated metal oxide was manufactured or stabilized in dispersion. The alkali metal cations may be present in the interior portions of the particles, as well as on the surface of the particles. "Free alkali metal cation" refers to an alkali metal cation that is solubilized in the aqueous phase of a dispersion of colloidal silica, or that is present at the surface of the metal oxide particle, and does not refer to alkali metal cations that may be bound or trapped within the interior of the metal oxide particles and, thus, are inaccessible to the aqueous phase. The "total alkali metal cation" content refers to the total sum of any free alkali metal cations and any alkali metal cations present in the interior portions of the particles.

The metal oxide particles contain substantially no free alkali metal cations. For example, the metal oxide particles have a content of free alkali metal cations of about 0.2 wt. % or less (e.g., about 0.15 wt. % or less, about 0.1 wt. % or less, about 0.05 wt. % or less, about 0.03 wt. % or less, or about 0.01 wt. % or less). Methods by which the free alkali metal cation content of the particles can be reduced are discussed herein with respect to other aspects of the invention.

The metal oxide particles are subjected to surface treatment with a first hydrophobicity-imparting agent and, optionally, a second hydrophobicity-imparting agent to render the surface of the metal oxide particles hydrophobic. Without wishing to be bound by any particular theory, it is believed that the hydrophobicity-imparting agent reacts with the surface hydroxyl groups on the surface of the metal oxide particles to effectively replace the hydrophilic groups with other, hydrophobic, chemical groups.

"Hydrophobic" metal oxide particles, as the term is used herein, encompass varying levels or degrees of hydrophobicity. The degree of hydrophobicity imparted to the metal oxide particles will vary depending upon the type and amount of treating agent used. Hydrophobic metal oxide particles according to the invention preferably, but not necessarily, have about 25% or more (e.g., about 35% or more, about 45% or more, or about 50% or more) of the available metal oxide surface hydroxyl groups reacted. Generally, the hydrophobic metal oxide particles according to the invention have about 85% or less (e.g., about 75% or less, or about 65% or less) of the available metal oxide surface hydroxyl groups reacted.

The first hydrophobicity-imparting agent can be any suitable hydrophobicity-imparting agent, preferably capable of reacting with and/or replacing silanol groups on the surface of the metal oxide particles with hydrophobic chemical groups. For example, the first hydrophobicity-imparting agent can be an alkoxysilane compound. The alkoxysilane compound can be a monoalkoxysilane compound, dialkoxysilane compound, or trialkoxysilane compound. Alkoxysilanes include compounds having the general formula: $R^1_xSi(OR^2)_{4-x}$, wherein $R^1$ is selected from the group consisting of $C_1$-$C_{30}$ branched and straight chain alkyl, aminoalkyl, alkenyl, and aminoalkenyl, $C_3$-$C_{10}$ cycloalkyl, and $C_6$-$C_{10}$ aryl; $R^2$ is $C_1$-$C_{10}$ branched and straight chain alkyl; and x is an integer from 1 to 3. Suitable alkoxysilane compounds include, for example, trimethylmethoxysilane, dimethyldimethoxysilane, methyltrimethoxysilane, and the like.

Preferably, the alkoxysilane compound is a trialkoxysilane compound. The trialkoxysilane compound can be any suitable trialkoxysilane compound. For example, the trialkoxysilane compound can have the formula: $R^1Si(OR^2)_3$, wherein $R^1$ is selected from the group consisting of $C_1$-$C_{30}$ branched and straight chain alkyl, aminoalkyl, alkenyl, and aminoalkenyl, and $C_3$-$C_{10}$ cycloalkyl, and $R^2$ is $C_1$-$C_{10}$ branched or straight chain alkyl. Preferably, the trialkoxysilane compound is selected from the group consisting of methyltrimethoxysilane, ethyltrimethoxysilane, propyltrimethoxysilane, butyltrimethoxysilane, pentyltrimethoxysilane, hexyltrimethoxysilane, heptyltrimethoxysilane, octyltrimethoxysilane, nonyltrimethoxysilane, decyltrimethoxysilane, undecyltrimethoxysilane, dodecyltrimethoxysilane, tetradecyltrimethoxysilane, stearyltrimethoxysilane, methyltriethoxysilane, ethyltriethoxysilane, propyltriethoxysilane, butyltriethoxysilane, pentyltriethoxysilane, hexyltriethoxysilane, heptyltriethoxysilane, nonyltriethoxysilane, decyltriethoxysilane, undecyltriethoxysilane, dodecyltriethoxysilane, tetradecyltriethoxysilane, stearyltriethoxysilane, and combinations thereof. More preferably, the trialkoxysilane compound is selected from the group consisting of propyltrimethoxysilane, hexyltrimethoxysilane, heptyltrimethoxysilane, octyltrimethoxysilane, nonyltrimethoxysilane, decyltrimethoxysilane, undecyltrimethoxysilane, dodecyltrimethoxysilane, tetradecyltrimethoxysilane, stearyltrimethoxysilane, methyltriethoxysilane, ethyltriethoxysilane, propyltriethoxysilane, butyltriethoxysilane, pentyltriethoxysilane, hexyltriethoxysilane, heptyltriethoxysilane, octyltriethoxysilane, nonyltriethoxysilane, decyltriethoxysilane, undecyltriethoxysilane, dodecyltriethoxysilane, tetradecyltriethoxysilane, stearyltriethoxysilane, 3-aminopropyltriethoxysilane, 3-aminobutyltriethoxysilane, 3-aminobutyltriethoxysilane, and combinations thereof. Most preferably, the trialkoxysilane compound is octyltriethoxysilane. The first hydrophobicity-imparting agent also can comprise mixtures of any of the foregoing.

The metal oxide particles can be treated with a second hydrophobicity-imparting agent. The second hydrophobicity-imparting agent can be any suitable hydrophobicity-imparting agent, preferably capable of reacting with and/or replacing silanol groups on the surface of the metal oxide particles with hydrophobic chemical groups. The second hydrophobicity-imparting agent can be an aza-silane (i.e., a cyclic silane compound that contains a Si—N—C bond), an aminoalkylsilane (e.g., aminopropylsilane), or a silazane. The silazane can be any suitable silazane. For example, the silazane can be a monosilazane or a disilazane. Preferably, the silazane is hexamethyldisilazane (HMDZ). The second hydrophobicity-imparting agent also can comprise mixtures of any of the foregoing.

The treated metal oxide particles can have any suitable average non-agglomerated particle size. The particle size refers to the diameter of the smallest sphere that encloses the non-agglomerated particle. Agglomerated particles (agglomerates) are composed of several primary particles loosely attached to each other, usually by van der Waals forces. This is in contrast to aggregated particles (aggregates), in which the bonds between primary particles are stronger, as is the case when the particles sinter. As a result, de-agglomeration can be easily achieved for agglomerates. For example, dispersion of treated metal oxide particles with toner particles (dry dispersion) or in a suitable liquid (e.g., tetrahydrofuran (THF)) using high speed agitation or sonication can be used to reverse agglomeration. However, it is considerably more difficult or even impossible to reverse aggregation to any significant extent.

Typically, the treated metal oxide particles have a non-agglomerated average particle size of about 5 nm or more (e.g., about 10 nm or more, about 15 nm or more, about 20 nm or more, or about 30 nm or more) and, generally, about 300 nm or less (e.g., about 250 nm or less, about 200 nm or less, about 150 nm or less, about 130 nm or less, or about 100 nm or less). According to one aspect of the invention, the non-agglomerated average particle size of the metal oxide particles is less than about 100 nm (e.g., about 90 nm or less, about 75 nm or less, or about 50 nm or less). Accordingly, the average particle size of the non-agglomerated metal oxide particles can be about 5 nm to about 300 nm (e.g., about 10 nm to about 100 nm, about 20 nm to about 80 nm, about 30 nm to about 70 nm, or about 40 nm to about 60 nm).

The treated metal oxide particles preferably have a BET surface area of about 200 $m^2$/g or less (determined by the method of S. Brunauer, P. H. Emmet, and I. Teller, *J. Am. Chemical Society*, 60, 309 (1938), which is commonly referred to as the BET method). Typically, the metal oxide particles have a BET surface area of about 15 $m^2$/g or more (e.g., about 20 $m^2$/g or more, about 25 $m^2$/g or more, about 30 $m^2$/g or more, about 40 $m^2$/g or more, about 50 $m^2$/g or more, about 55 $m^2$/g or more, or about 60 $m^2$/g or more). The BET surface area of the metal oxide particles typically will be about 200 $m^2$/g or less, more typically about 180 $m^2$/g or less (e.g., about 160 $m^2$/g or less, about 140 $m^2$/g or less, about 130 $m^2$/g or less, about 120 $m^2$/g or less, about 100 $m^2$/g or less, about 80 $m^2$/g or less, about 65 $m^2$/g or less, about 60 $m^2$/g or less, about 50 $m^2$/g or less, or about 40 $m^2$/g or less). Preferably, the BET surface area of the metal oxide particles is about 15 $m^2$/g to about 200 $m^2$/g, and more preferably about 20 $m^2$/g to about 180 $m^2$/g (e.g., about 20 $m^2$/g to about 160 $m^2$/g, about 20 $m^2$/g to about 100 $m^2$/g, about 20 $m^2$/g to about 80 $m^2$/g, about 20 $m^2$/g to about 65 $m^2$/g, or about 20 $m^2$/g to about 55 $m^2$/g).

The treated metal oxide particles can have any suitable tap density. The tap density of the treated metal oxide particles can be determined using a tap volumeter (3000 taps) and the following equation: tap density (g/L)=(weight of the treated metal oxide particles (g))×(1000/(volume (ml) of the treated metal oxide particles)).

The tap density of the treated metal oxide particles typically will be about 650 g/L or less, more typically about 600 g/L or less (e.g., about 550 g/L or less, about 500 g/L or less, about 420 g/L or less, about 400 g/L or less, about 350 g/L or less, about 290 g/L or less, about 250 g/L or less, about 230 g/L or less, or about 180 g/L or less). The tap density of the metal oxide particles typically will be about 75 g/L or more (e.g., about 85 g/L or more, about 95 g/L or more, about 100 g/L or more, about 125 g/L or more, or about 135 g/L or more). Accordingly, the tap density of the metal oxide particles is about 75 g/L to about 650 g/L (e.g., about 110 g/L to about 420 g/L, about 290 g/L to about 650 g/L, about 290 g/L to about 420 g/L, about 300 g/L to about 420 g/L, or about 420 g/L to about 650 g/L).

The metal oxide particles (e.g., hydrophilic particles) can have any suitable true density. Typically, the metal oxide particles have a true density of about 1.5 g/cm$^3$ or more (e.g., about 1.7 g/cm$^3$ or more, about 2.0 g/cm$^3$ or more, or about 2.2 g/cm$^3$ or more). The true density of the metal oxide particles typically will be about 5 g/cm$^3$ or less, more typically about 4 g/cm$^3$ or less (e.g., about 3.5 g/cm$^3$ or less, about 3 g/cm$^3$ or less, about 2.8 g/cm$^3$ or less, about 2.5 g/cm$^3$ or less, or about 2.3 g/cm$^3$ or less). Preferably, the true density of the metal oxide particles is about 1.5 g/cm$^3$ to about 5 g/cm$^3$, and more preferably about 1.5 g/cm$^3$ to about 4 g/cm$^3$ (e.g., about 1.5 g/cm$^3$ to about 3.5 g/cm$^3$, about 1.5 g/cm$^3$ to about 3 g/cm$^3$, about 1.8 g/cm$^3$ to about 2.8 g/cm$^3$, about 2 g/cm$^3$ to about 2.5 g/cm$^3$, or about 2.2 g/cm$^3$ to about 2.4 g/cm$^3$). More preferably, the true density of the metal oxide particles is about 1.7 g/cm$^3$ to about 2.0 g/cm$^3$, or about 2.0 g/cm$^3$ to about 2.3 g/cm$^3$.

The carbon content of the treated metal oxide particles can be used as an indicator of the level of treatment of the treated metal oxide particles and, thus, as an indicator of the degree of hydrophobicity. The carbon content of the treated particles can be determined using commercially available carbon analyzers (e.g., Leco C-200). The treated metal oxide particles prepared in accordance with the invention desirably have a carbon content of about 0.1 wt. % or more (e.g., about 0.15 wt. % or more, about 0.2 wt. % or more, about 0.25 wt. % or more, about 0.3 wt. % or more, about 0.4 wt. % or more, or about 0.5 wt. % or more). The carbon content of the treated metal oxide particles typically comprises less than about 8 wt. % (e.g., about 7 wt. % or less, about 6 wt. % or less, about 5 wt. % or less, about 4 wt. % or less, or about 3 wt. % or less). Thus, the carbon content of the treated metal oxide particles can be, for example, from about 0.1 wt. % to about 8 wt. % (e.g., from about 0.15 wt. % to about 6 wt. %, from about 0.15 wt. % to about 4 wt. %, from about 0.15 wt. % to about 2 wt. %, from about 1 wt. % to about 4 wt. %, from about 2 wt. % to about 5 wt. %, from about 3 wt. % to about 6 wt. %, or from about 4 wt. % to about 8 wt. %).

The surface treatment of the metal oxide particles (e.g., hydrophilic particles) with a first hydrophobicity-imparting agent according to the invention can generate various patterns of substituted silicon atoms attached to the surface of the metal oxide particles or attached indirectly to the surface of the metal oxide particles. These substitution patterns have been referred to in the literature as M sites, D sites, T sites, and Q sites. See, for example, Sindorf, Dean William, "Silicon-29 and Carbon-13 CP/MAS NMR Studies of Silica Gel and Bonded Silane Phases," Department of Chemistry, Colorado State University, Fort Collins, Colo., 1982. The correlation of the M sites, D sites, T sites, and Q sites to the resonance signals in the CP/MAS $^{29}$Si NMR spectrum also is discussed in Maciel, G., Sindorf, D. W., *J. Am. Chem. Soc.*, 102: 7607-7608 (1980), Sindorf, D. W., Maciel, G., *J. Phys. Chem.*, 86: 5208-5219 (1982), and Sindorf, D. W., Maciel, G., *J. Am. Chem. Soc.*, 105: 3767-3776 (1983).

In accordance with one embodiment of the invention, the surface treatment of the metal oxide particles (e.g., hydrophilic particles) with a first hydrophobicity-imparting agent provides metal oxide particles having predominant substitution patterns referred to as T2 and T3 sites. As used herein, T2 sites correspond to a silicon atom originating from the first hydrophobicity-imparting agent having two bonds to oxygen atoms further bonded to silicon atoms, at least one of which is on the metal oxide particle surface, one bond to an oxygen atom comprising a silanol (Si—OH) group, and one bond to a carbon atom. T2 sites are represented by formula (I): R—Si(OH)—(OSi—P$^1$)(OSiP$^2$) wherein R is as defined herein for the hydrophobicity-imparting agent, and P$^1$ and P$^2$ independently represent a bond to a silicon atom on a particle surface and/or a silicon atom of another silane-containing molecule. Si atoms corresponding to T2 sites have been correlated with the resonance signals with chemical shifts in the range from −56 ppm to −59 ppm in the CP/MAS $^{29}$Si NMR spectrum, wherein the chemical shift in ppm is measured relative to the standard tetramethylsilane.

As used herein, T3 sites correspond to a silicon atom originating from the first hydrophobicity-imparting agent having three bonds to an oxygen atom further bonded to silicon atoms. At least one of the silicon atoms is a silicon atom on a metal oxide particle. The sites are represented by the formula (II): R—Si(OSi—P$^1$)(OSi—P$^2$)(OSi—P$^3$), wherein R is as herein defined for the hydrophobicity-imparting agent, and P$^1$, P$^2$, and P$^3$ independently represent a bond to a silicon atom on a particle surface and/or a silicon atom of another silane-containing molecule. Si atoms corresponding to T3 sites have been correlated with the resonance signals with chemical shifts in the range from −65 ppm to −69 ppm in the CP/MAS $^{29}$Si NMR spectrum, wherein the chemical shift in ppm is measured relative to the standard tetramethylsilane.

The treated metal oxide particles of the invention preferably have substitution patterns resulting in CP/MAS $^{29}$Si NMR peak intensities for T3 and T2 that have a ratio of T3 to T2 (i.e., T3:T2) of about 0.4 to about 10, wherein T3 and T2 are as defined herein. The ratio of T3:T2 depends, at least in part, on the particular reaction conditions, such as the pH, employed in the preparation of the treated metal oxide particles. As defined herein, T2 is the integrated intensity of a peak having a chemical shift in the CP/MAS $^{29}$Si NMR spectrum centered within the range of −56 ppm to −59 ppm. T3 is the integrated intensity of a peak having a chemical shift in the CP/MAS $^{29}$Si NMR spectrum centered within the range of −65 ppm to −69 ppm. The intensity of a peak refers to the maximum peak height of the signal at that approximate location or the area of the peak occurring within the recited ranges, as calculated using standard calculation methods well known to those skilled in the art.

The particle composition can be formulated as a dry particle composition (e.g., a dry powder) or as a wet particle composition (e.g., a dispersion) comprising the treated metal oxide particles. The dispersion can comprise any suitable dispersant, preferably water alone or water with a co-solvent, treating agent(s), or additive(s) of any type commonly used in dispersions of hydrophobic metal oxide particles.

The treated metal oxide particles can be used for many different applications including, but not limited to, toner compositions, antiblocking agents, adhesion modifiers, polymer additives (e.g., for elastomers and rubbers, such as silicone rubbers), abrasion-resistant coatings and films, delustering coatings and films, reological control agents (e.g., for epoxies or liquid polymers), and mechanical/optical control agents (e.g., for composites and plastics). The treated metal oxide particles are especially useful in toner compositions. In that regard, the invention provides a toner composition comprising toner particles and metal oxide particles surface-treated with a first hydrophobicity-imparting agent, and, optionally, a second hydrophobicity-imparting agent, which metal oxide particles are hydrophobic and contain substantially no free alkali metal cations.

All aspects of the treated metal oxide particles used in the toner composition are as described with respect to the metal oxide particles of the invention. Thus, the treated metal oxide particles can be non-aggregated particles. However, the metal oxide particles useful in the toner composition further comprise aggregated metal oxide particles treated with a first hydrophobicity-imparting agent, which metal oxide particles are hydrophobic and contain substantially no free alkali metal cations. Such metal oxide particles are otherwise as described herein with respect to the treated metal oxide particles of the invention, and can be prepared in accordance with the method of the invention.

Toner compositions containing the treated metal oxide particles can be formulated, for example, by mixing the treated particles (e.g., from about 1 wt. % of the treated particles to about 5 wt. % of the treated particles) in a blender with pulverized toner particles (e.g., styrene acrylate), preferably free of any external additives and having a suitable average diameter (e.g., 9 μm). Toner compositions containing the treated particles then can be developed, for example, by rolling in glass jars (e.g., rolling for 30 minutes at a 2/98 wt. % toner/carrier ratio). The carrier can be, for example, 70 μm Cu—Zn ferrite coated with silicone resin. Samples also can be conditioned in a standard humidity chamber at either a high humidity and high temperature (e.g., 30° C. and 80% relative humidity) or at a low humidity and low temperature (e.g., 18° C. and 15% relative humidity) overnight.

The treated metal oxide particles can be used in any suitable toner composition, including positively-charged and negatively charged toner compositions. Without wishing to be bound by a particular theory, it is thought that the presence of the treated metal oxide particles stabilizes and increases the absolute tribocharge value of toner compositions containing the metal oxide particles.

The tribocharge of toner compositions containing the treated metal oxide particles can be either positive or negative. Tribocharge measurements can be made using suitable techniques and equipment known in the art (e.g., Vertex T-150 tribocharger). Measurements can be made after conditioning the toner particles overnight in a standard humidity chamber at 30° C. and 80% relative humidity (HH) and at 18° C. and 15% relative humidity (LL). The toner particles (e.g., of a toner composition comprising about 4 wt. % treated metal oxide particles) preferably have a tribocharge at HH conditions of about −40 μC/g to about +15 μC/g (e.g., about −40 μC/g to about −20 μC/g, about −40 μC/g to about 0 μC/g, about −5 μC/g to about +10 μC/g, about 0 μC/g to about +5 μC/g, or about +5 μC/g to about +10 μC/g). The toner particles preferably have a tribocharge at LL conditions of about −100 μC/g to about +25 μC/g (e.g., about −80 μC/g to about −50 μC/g, about −80 μC/g to about 0 μC/g, about −5 μC/g to about +10 μC/g, about +5 μC/g to about +35 μC/g, or about +10 μC/g to about +25 μC/g).

In a preferred aspect of the invention, the treated metal oxide particles can be used to improve the free-flow characteristics of a toner composition. Without wishing to be bound by a particular theory, it is thought that the presence of the treated metal oxide particles, especially particles which have been jet milled, improves the free-flow of toner compositions containing the metal oxide particles due to the lower tap and bulk densities of the treated particles. In the context of the invention, free-flow is the percentage of toner discharged from a grounded metal role tube of 25 mm in diameter and 350 mm in length, with seven 0.5 mm discharge holes, that contains 40 g of the toner composition and is rotated at 30 rpm for one minute for a total of 30 rotations.

The toner composition comprising the treated metal oxide particles preferably has a free-flow of about 1 wt. % loss or more (e.g., about 1.5 wt. % loss or more, about 2 wt. % loss or more, about 2.5 wt. % loss or more, about 3 wt. % loss or more, or about 3.5 wt. % loss or more). The free-flow of the toner composition typically will be about 10 wt. % loss or less (e.g., about 8 wt. % loss or less, about 7 wt. % loss or less, about 6 wt. % loss or less, about 5 wt. % loss or less, or about 4 wt. % loss or less). Preferably, the free-flow of the toner composition is about 1 wt. % loss to about 10 wt. % loss (e.g., about 1 wt. % loss to about 8 wt. % loss, about 1 wt. % loss to about 7 wt. % loss, about 1 wt. % loss to about 6 wt. % loss, about 1 wt. % loss to about 5 wt. % loss, about 1 wt. % loss to about 4 wt. % loss, about 1.5 wt. % loss to about 8 wt. % loss, about 2 wt. % loss to about 8 wt. % loss, about 2.5 wt. % loss to about 8 wt. % loss, about 3 wt. % loss to about 8 wt. % loss, or about 3.5 wt. % loss to about 8 wt. % loss).

Also provided herein is a method of preparing hydrophobic metal oxide particles, which method comprises (a) providing an aqueous dispersion of metal oxide particles (e.g., hydrophilic particles), wherein the aqueous dispersion is acidic or basic, (b) combining the dispersion with a first hydrophobicity-imparting agent and, optionally, a second hydrophobicity-imparting agent to provide a reaction mixture, and (c) drying the reaction mixture to provide hydrophobic metal oxide particles, wherein the hydrophobic metal oxide particles contain substantially no free alkali metal cations. The first and second hydrophobicity-imparting agents are as described herein with respect to the treated metal oxide particles of the invention.

The aqueous dispersion of metal oxide particles preferably is colloidally stable. The colloidal stability of the dispersion prevents any substantial portion of the particles from irreversibly agglomerating or gelling, or from settling out of the dispersion during use. The aqueous dispersion of metal oxide particles used in conjunction with the invention preferably has a degree of colloidal stability such that the average overall particle size of the metal oxide in dispersion, as measured by dynamic light scattering, does not change over a period of 1 hour or more (e.g., about 8 hours or more, or about 24 hours or more), more preferably 2 weeks or more (e.g., about 4 weeks or more, or about 6 weeks or more), most preferably 8 weeks or more (e.g., about 10 weeks or more, or about 12 weeks or more), or even about even 16 weeks or more.

Before treatment, the aqueous dispersion of metal oxide particles can be acidic, i.e., can have a pH less than about 7, or basic, i.e., can have a pH greater than about 7. The pH of the dispersion can be, for example, about 12 or less (e.g., about 11 or less, about 10 or less, about 9 or less, about 8 or less, or about 7 or less). Generally, the pH of the reaction mixture will be about 1 or more (e.g., about 2 or more, about 3 or more, about 4 or more, about 5 or more, or about 6 or more). Thus, the pH of the dispersion can be, for example, from about 1 to about 12 (e.g., from about 1 to about 5, from about 1 to about 3.5, from about 1 to about 2.5, from about 7 to about 12, from about 8 to about 11, from about 9 to about 10.5, or from about 9.5 to about 10.5). The pH of the dispersion can be adjusted to desired levels, for example, by adding an acid or a base to the dispersion.

The aqueous dispersion of metal oxide particles can be provided by a commercially available dispersion of metal oxide particles (e.g., a commercially available colloidal metal oxide), several examples of which are disclosed above in connection with the particle composition of the invention. Alternatively, the aqueous dispersion of metal oxide particles can be prepared by any suitable method. For example, an aqueous dispersion of metal oxide particles can be prepared by dispersing silica particles in water, alone or with a co-solvent, using a high-shear mixer. The metal oxide particles can be of any type, including, but not limited to, wet-process metal oxides (e.g., precipitated metal oxides) and pyrogenically-produced metal oxides (e.g., fumed metal oxides). Alternatively, the aqueous dispersion of metal oxide particles can be prepared in solution from a metal oxide precursor. For example, an aqueous dispersion of silica particles can be prepared by adjusting the pH of metal silicate solution to about 9 to about 11, wherein the silicate anions provided by the metal silicate undergo polymerization to produce discrete silica particles having the desired average particle size in the form of an aqueous dispersion. Specific protocols and techniques for preparing aqueous dispersions of metal oxides in this manner and controlling the particle size of such dispersions (e.g., by adjusting temperature, concentration, and pH) are generally available in the art. Furthermore, other suitable methods of providing an aqueous dispersion of metal oxide particles are known in the art, any of which can be used in conjunction with the invention. Preferably, the aqueous dispersion of metal oxide particles is an aqueous dispersion of colloidal metal oxide particles, especially colloidal silica particles.

Whether provided by a commercially available product, or provided in some other manner, the aqueous dispersion of metal oxide particles may contain free alkali metal cations as a result of the manufacture or stabilization of the dispersion. The free alkali metal cation can be sodium, potassium, or any other Group I metal cation. The free alkali metal cation content of the metal oxide dispersion can be reduced, for example, by treatment of the dispersion with an acidic ion exchange resin. Alternatively, or in addition, the free alkali metal cation content of the base-stabilized dispersion of metal oxide particles can be reduced by using ultrafiltration, e.g., difiltration. Reduction of the free alkali metal cation content also may reduce the pH of the dispersion. If desired, the pH can be adjusted without increasing the free alkali metal content by addition of an amine or by addition of ammonium hydroxide ($NH_4OH$). It is also possible to avoid the need to reduce the alkali metal cation content of the dispersion, in accordance with this preferred aspect of the invention, by using an ammonium-stabilized aqueous dispersion of metal oxide as a starting material.

Reduction of the free alkali metal cation content of the aqueous dispersion of metal oxide, to the extent it is required, can be performed at any time before or after the first and/or second hydrophobicity-imparting agent is added to the aqueous dispersion of metal oxide. For example, the free alkali metal cation reducing treatment (e.g., ion exchange, ultrafiltration, or the like) can be performed as part of the production process of the metal oxide dispersion, or can be performed on a commercially available aqueous dispersion of metal oxide before use in the invention (e.g., about 1 hour or less before use, or about 1 day or less before use, or about 1 week or less before use). Alternatively, the free alkali metal cation reducing treatment can be employed after one or both of the first hydrophobicity-imparting agent and second hydrophobicity-imparting agent is combined with the dispersion of metal oxide particles. Instead, or in addition, the free alkali metal cation reducing treatment also can be used to reduce the alkali metal content of the treated metal oxide particles at a later time, for example, by dispersing dried, treated metal oxide particles in water or an acceptable solvent and reducing the free alkali metal content of the dispersion, after which the treated metal oxide particles can be isolated and/or dried by any suitable method.

Desirably, when the dispersion is combined with the first hydrophobicity-imparting agent, the dispersion can be combined with an organic solvent. The organic solvent can be any suitable organic solvent. Preferably, the organic solvent is water-soluble or water-miscible. More preferably, the organic solvent is water-soluble. The water-soluble organic solvent can be any suitable water-soluble organic solvent, such as an alcohol (e.g., methanol, ethanol, n-propanol, 2-propanol, n-butanol, isobutanol, sec-butanol, tert-butanol, n-propanol, ethylene glycol, and propylene glycol), ketone (e.g., acetone and 2-butanone), ether (e.g., tetrahydrofuran and 1,2-dimethoxyethane), and combinations thereof. The water and water-soluble organic solvent can be added in any order. For example, the water can be added before the water-soluble organic solvent, or vice versa. Desirably, the water is added first, to reduce the concentration of solids to a suitable amount before addition of the water-soluble organic solvent, especially when using a base-stabilized dispersion. Although not wishing to be bound by a particular theory, it is thought that adding the water before the water-soluble organic solvent prevents the dispersion from gelling.

Alternatively, when the dispersion is combined with the first hydrophobicity-imparting agent, the dispersion need not be combined with an organic solvent. More specifically, the treatment of the metal oxide particles with the first hydrophobicity-imparting agent in water is effective without an organic solvent.

The first hydrophobicity-imparting agent, optional second hydrophobicity-imparting agent, and organic solvent, when used, can be added to the dispersion in any order. The organic solvent can be added before the first and/or second hydrophobicity-imparting agents, or vise versa. Desirably, the organic solvent is added to the dispersion before contacting the metal oxide particles with the first and/or second hydrophobicity-imparting agent. Without wishing to be bound by a particular theory, it is thought that adding the organic solvent to the initial dispersion, before the addition of the first and/or second hydrophobicity-imparting agent, results in a treated metal oxide particle that, when used in a toner composition, has a greater impact on tribocharge. Typically, the reaction mixture will comprise no more than about 50 wt. % of organic solvent, and preferably will comprise not more than about 40 wt. % of organic solvent.

When the dispersion is combined with a water-soluble organic solvent, the water-soluble organic solvent to water volume ratio can be any suitable ratio. The ratio typically is less than about 10 (e.g., about 8 or less, about 6 or less, about 5 or less, about 3 or less, about 2 or less, or about 1 or less).

The ratio can be about 0.05 or more (e.g., about 0.1 or more, about 0.5 or more, about 0.7 or more, about 1 or more, or about 1.2 or more), such as about 0.05 to about 10 (e.g., from about 0.1 to about 5, or from about 0.2 to about 2).

The aqueous dispersion containing the metal oxide particles (e.g., hydrophilic particles) can contain any suitable amount of metal oxide particles. The aqueous dispersion typically comprises about 45 wt. % or less (e.g., about 35 wt. % or less, about 25 wt. % or less, about 15 wt. % or less, about 10 wt. % or less, or about 5 wt. % or less) metal oxide particles. The aqueous dispersion can comprise about 5 wt. % or more (e.g., about 10 wt. % or more, about 15 wt. % or more, about 20 wt. % or more, about 25 wt. % or more, or about 30 wt. % or more) metal oxide particles. Thus, the aqueous dispersion can comprise, for example, from about 5 wt. % to about 45 wt. % (e.g., from about 10 wt. % to about 45 wt. %, from about 15 wt. % to about 35 wt. %, or from about 15 wt. % to about 20 wt. %) metal oxide particles.

The amount of the first hydrophobicity-imparting agent that is added to the aqueous dispersion containing the hydrophilic metal oxide particles can be any suitable amount. The amount of the first hydrophobicity-imparting agent typically comprises less than about 50 $\mu$mole/m$^2$ metal oxide particles (e.g., less than about 40 $\mu$mole/m$^2$, less than about 30 $\mu$mole/m$^2$, less than about 25 $\mu$mole/m$^2$, less than about 20 $\mu$mole/m$^2$, less than about 15 $\mu$mole/m$^2$, or less than about 10 $\mu$mole/m$^2$). The amount of the first hydrophobicity-imparting agent can comprise about 0.1 $\mu$mole/m$^2$ metal oxide particles or more (e.g., about 0.25 $\mu$mole/m$^2$ or more, about 0.5 $\mu$mole/m$^2$ or more, about 1 $\mu$mole/m$^2$ or more, about 1.5 $\mu$mole/m$^2$ or more, or about 2 $\mu$mole/m$^2$ or more). Thus, the amount of the first hydrophobicity-imparting agent can comprise, for example, from about 0.1 $\mu$mole/m$^2$ metal oxide particles to about 50 $\mu$mole/m$^2$ metal oxide particles (e.g., from about 0.1 $\mu$mole/m$^2$ to about 10 $\mu$mole/m$^2$, from about 1 $\mu$mole/m$^2$ to about 15 $\mu$mole/m$^2$, from about 5 $\mu$mole/m$^2$ to about 25 $\mu$mole/m$^2$, or from about 15 $\mu$mole/m$^2$ to about 40 $\mu$mole/m$^2$).

The amount of the second hydrophobicity-imparting agent that is added to the aqueous dispersion containing the hydrophilic metal oxide particles can be any suitable amount. The amount of the second hydrophobicity-imparting agent typically comprises less than about 50 $\mu$mole/m$^2$ metal oxide particles (e.g., less than about 40 $\mu$mole/m$^2$, less than about 30 $\mu$mole/m$^2$, less than about 25 $\mu$mole/m$^2$, less than about 20 $\mu$mole/m$^2$, less than about 15 $\mu$mole/m$^2$, or less than about 10 $\mu$mole/m$^2$). The amount of the second hydrophobicity-imparting agent can comprise about 0.1 $\mu$mole/m$^2$ metal oxide particles or more (e.g., about 0.25 $\mu$mole/m$^2$ or more, about 0.5 $\mu$mole/m$^2$ or more, about 1 $\mu$mole/m$^2$ or more, about 1.5 $\mu$mole/m$^2$ or more, or about 2 $\mu$mole/m$^2$ or more). Thus, the amount of the second hydrophobicity-imparting agent can comprise, for example, from about 0.1 $\mu$mole/m$^2$ metal oxide particles to about 50 $\mu$mole/m$^2$ metal oxide particles (e.g., from about 0.1 $\mu$mole/m$^2$ to about 10 $\mu$mole/m$^2$, from about 1 $\mu$mole/m$^2$ to about 15 $\mu$mole/m$^2$, from about 5 $\mu$mole/m$^2$ to about 25 $\mu$mole/m$^2$, or from about 15 $\mu$mole/m$^2$ to about 40 $\mu$mole/m$^2$).

The reaction mixture can be maintained at any temperature and for a sufficient period of time to allow the first and/or second hydrophobicity-imparting agent to react completely, or to any extent desired, with the aqueous dispersion of the metal oxide particles (e.g., react with the silanol groups on the surface of the silica particles). Generally, the reaction mixture is maintained at a temperature of about 20° C. to about 100° C. (e.g., about 30° C. to about 90° C., about 40° C. to about 80° C., or about 55° C. to about 70° C.), for about 5 minutes or longer (e.g., about 10 minutes or longer, or about 30 minutes or longer), or even about 60 minutes or longer (e.g., about 120 minutes or longer, about 180 minutes or longer, or about 240 minutes or longer). Longer reaction times (e.g., about 5 hours or longer, about 7 hours or longer, about 10 hours or longer, or about 20 hours or longer) may be required depending upon particular reaction conditions (e.g., temperature and concentration of reagents).

The reaction mixture can be contained in an open or closed reactor. While the reaction mixture can be maintained in an atmosphere of air, oxygen can be excluded from the reaction atmosphere, in which event the reaction mixture can be maintained under an atmosphere consisting essentially of nitrogen, argon, or a mixture thereof.

The first and/or second hydrophobicity imparting agent can be combined with the aqueous dispersion in any suitable manner. The aqueous dispersion of metal oxide particles can be combined with the first hydrophobicity-imparting agent to provide a first reaction mixture, and the first reaction mixture can be maintained at any temperature and for a sufficient time to allow the first hydrophobicity-imparting agent to react with the aqueous dispersion of metal oxide particles as described herein. Generally, the first reaction mixture is maintained at a temperature of about 20° C. to about 80° C. (e.g., about 40° C. to about 80° C., about 45° C. to about 65° C., or about 45° C. to about 55° C.) for about 1 hour or longer (e.g., about 1 hour to about 24 hours, about 3 hours to about 20 hours, or about 4 hours to about 12 hours). Typically, treatment time for the first reaction mixture is between about 4 hours and about 12 hours (e.g., about 5 hours to about 10 hours, or about 6 hours to about 8 hours).

The second hydrophobicity-imparting agent can then be added to the first reaction mixture to provide a second reaction mixture, and the second reaction mixture can be maintained at any temperature and for a sufficient time to allow the second hydrophobicity-imparting agent to react with the aqueous dispersion of metal oxide particles as described herein. Generally, the second reaction mixture is maintained at a temperature of about 30° C. to about 80° C. (e.g., about 40° C. to about 80° C., about 45° C. to about 65° C., or about 45° C. to about 55° C.) for about 1 hour or longer (e.g., about 1 hour to about 24 hours, about 3 hours to about 20 hours, or about 4 hours to about 12 hours). Typically, treatment time for the second reaction mixture is between about 2 hours and about 5 hours (e.g., about 2.5 hours to about 4.5 hours, or about 3 hours to about 4 hours). Desirably, the pH of the second reaction mixture is from about 7 to about 12 (e.g., about 8 to about 11, or about 9 to about 10).

Alternatively, the aqueous dispersion is combined with the second hydrophobicity-imparting agent to provide a first reaction mixture. According to this embodiment, the first hydrophobicity-imparting agent is subsequently added to the first reaction mixture to provide a second reaction mixture.

In yet another alternative, the first and second hydrophobicity-imparting agents can be combined simultaneously, or substantially simultaneously, with the aqueous dispersion to provide a reaction mixture. For example, the components can be combined simultaneously, or stepwise, to a reaction vessel containing the aqueous dispersion of metal oxide particles so that not more than 5 minutes (e.g., not more than 10 minutes, or not more than 30 minutes) elapses between addition of the two components. Desirably, the pH of the reaction mixture is about 7 or more (e.g., about 8 or more, or about 9 or more). Preferably, the pH of the reaction mixture is about 12 or less (e.g., about 11 or less, or about 10 or less). Thus, the pH of the reaction mixture is from about 7 to about 12 (e.g., about 8 to about 11, or about 9 to about 10). Generally, the reaction mixture is maintained at a temperature of about 50° C. to about 75° C. (e.g., about 50° C. to about 70° C., or about 65° C. to about 75° C.) for about 2 hours to about 24 hours (e.g., about 5 hours to about 20 hours, about 8 hours to about 12 hours, or about 9 hours to about 11 hours).

After treatment with the first and/or second hydrophobicity-imparting agent, the metal oxide particles preferably are isolated from the reaction mixture and dried. The hydrophobic metal oxide particles can be dried after isolation from the reaction mixture, or directly from the reaction mixture, by evaporating the volatile components of the reaction mixture from the hydrophobic metal oxide particles. Evaporation of the volatile components of the reaction mixture can be accomplished using any suitable techniques, e.g., heat and/or reduced atmospheric pressure. When heat is used, the hydrophobic metal oxide particles can be heated to any suitable drying temperature, for example, by using an oven or other similar device, or by spray drying.

Spray drying involves spraying the reaction mixture, or some portion thereof, comprising the hydrophobic metal oxide particles as a fine mist into a drying chamber, wherein the fine mist is contacted with hot air causing the evaporation of volatile components of the reaction mixture.

The drying temperature chosen will depend, at least in part, on the specific components of the reaction mixture that require evaporation. Typically, the drying temperature will be about 40° C. or higher (e.g., about 50° C. or higher) such as about 70° C. or higher (e.g., about 80° C. or higher) or even about 120° C. or higher (e.g., about 130° C. or higher). Thus, the drying temperatures fall generally within the range of about 40° C. to about 250° C. (e.g., about 50° C. to about 200° C.), such as about 60° C. to about 200° C. (e.g., about 70° C. to about 175° C.), or about 80° C. to about 150° C. (e.g., about 90° C. to about 130° C.).

The hydrophobic metal oxide particles can be dried at any pressure that will provide a useful rate of evaporation. When drying temperatures of about 120° C. and higher (e.g., about 120° C. to about 150° C.) are used, drying pressures of about 125 kPa or less (e.g., about 75 kPa to about 125 kPa) are suitable. At drying temperatures lower than about 120° C. (e.g., about 40° C. to about 120° C.), drying pressures of about 100 kPa or less (e.g., about 75 kPa or less) are useful. Of course, reduced pressure (e.g., pressures of about 100 kPa or less, 75 kPa or less, or even 50 kPa or less) can be used as a sole method for evaporating the volatile components of the reaction mixture.

Alternatively, the hydrophobic metal oxide particles can be dried by lyophilization, wherein the liquid components of the reaction mixture are converted to a solid phase (i.e., frozen) and then to a gas phase by the application of a vacuum. For example, the reaction mixture comprising the hydrophobic metal oxide particles can be brought to a suitable temperature (e.g., about −20° C. or less, or about −10° C. or less, or even −5° C. or less) to freeze the liquid components of the reaction mixture, and a vacuum can be applied to evaporate those components of the reaction mixture to provide dry hydrophobic metal oxide particles.

The hydrophobic metal oxide particles can be washed prior to or after isolation and/or drying from the reaction mixture. Washing the treated metal oxide particles can be performed using a suitable washing solvent, such as water, a water-miscible organic solvent, a water-immiscible solvent, or a mixture thereof. The washing solvent can be added to the reaction mixture and the resulting mixture suitably mixed, followed by filtration, centrifugation, or drying to isolate the washed treated metal oxide particles. Alternatively, the treated metal oxide particles can be isolated from the reaction mixture prior to washing. The washed treated metal oxide particles can be further washed with additional washing steps followed by additional filtration, centrifugation, and/or drying steps.

The hydrophobic metal oxide particles have a particle size that is dependent, at least in part, on the particle size of the metal oxide particles in the initial dispersion. Preferred average particle sizes of the hydrophobic metal oxide particles prepared in accordance with the method of the invention are as described with respect to the treated metal oxide particles of the invention. Desirably, the average particle size of the hydrophobic, non-aggregated particles prepared in accordance with the method of the invention is within about 50%, preferably within about 30% (e.g., within about 20%, about 15%, about 10%, or even about 5%) of the average particle size of the metal oxide particles of the starting dispersion.

Preferably, the particle size of the hydrophobic metal oxide particles is further reduced after drying. Suitable processes for the reduction of the particle size of the treated metal oxide particles include but are not limited to wet or dry grinding, hammer milling, and jet milling.

All other aspects of the inventive method of preparing hydrophobic, non-aggregated metal oxide particles and resulting products are as discussed herein with respect to the treated metal oxide particles of the invention.

EXAMPLES

The following examples further illustrate the invention but, of course, should not be construed as in any way limiting its scope.

In each of the following examples, the hydrophobic metal oxide particles were prepared by treating an aqueous dispersion of commercially available colloidal silica particles with a first hydrophobicity-imparting agent and optionally a second hydrophobicity-imparting agent. The examples employ HMDZ and/or OTES as hydrophobicity-imparting agents, as specified.

The commercially available colloidal silica particles used in the examples are summarized in Table 1. Unless otherwise specified, treatment of the colloidal silica particles was carried out in an appropriately sized 3-neck round-bottom flask equipped with an overhead stirring motor, thermocouple, and condenser.

TABLE 1

| Dispersion | Wt. % Silica in Dispersion | pH | Surface Area After Drying (m$^2$/g) | Particle Size (nm) |
|---|---|---|---|---|
| Nissan MP 1040 | 40 | 9.6 | 25 | 101 |
| SNOWTEX YL | 40 | 9.6 | 34 | 83 |
| SNOWTEX OYL | 20 | 2 | 34 | 70 |
| SNOWTEX XL | 40 | 9.6 | 45 | 52 |
| SNOWTEX OL-20 | 20 | 2 | 60 | 45 |
| SNOWTEX OL-40 | 40 | 2 | 60 | 45 |
| SNOWTEX ZL | 40 | 9.3 | 30 | 85 |
| SNOWTEX OZL | 40 | 2 | 30 | 85 |

*OYL, OL, and OZL are ion-exchanged aqueous dispersions of colloidal silica.

The toner compositions referenced in the following examples were prepared by mixing 4 wt. % of the treated silica particles in a laboratory blender with a pulverized styrene acrylate black toner (9 μm average diameter) free of any external additives, followed by rolling for 30 minutes at a 2/98 wt. % toner/carrier ratio in glass jars. The carrier was 70 μm Cu—Zn ferrite coated with silicone resin. Samples were conditioned in a standard humidity chamber at either a high humidity and high temperature (30° C. and 80% relative humidity) ("HH") or at a low humidity and low temperature (18° C. and 15% relative humidity) ("LL") overnight. Tribocharge measurements were taken using a Vertex T-150 tribocharger.

Example 1

This example demonstrates the effect of the free alkali metal cation content of the treated metal oxide particles on the tribocharge of toner compositions comprising the treated metal oxide particles.

Two treated silica compositions (Compositions 1A and 1B) were prepared as follows: 100 g of the silica dispersion indicated in Table 2 was added to the reaction vessel. HMDZ was added to the dispersion in the amount indicated in Table 2, and the mixture was stirred rapidly at 50-55° C. at a rate such that the vortex of the dispersion extended at least to the top of the agitator blade. The mixture was allowed to react for 8 hours. The mixture was then poured into a glass dish and dried in a forced-air oven at 120-130° C.

The carbon content of the dried particles before and after extraction with toluene is presented in Table 2. Extraction was a Soxhlet extraction using 0.5-2 g of silica and approximately 100 ml toluene.

Toner compositions were prepared using the treated particles in the manner previously described. The tribocharge values of the toner compositions are also provided in Table 2.

TABLE 2

| Composition | Silica | HMDZ (μmole/m$^2$) | Carbon Content (wt. %) | Carbon Content After Extraction (wt. %) | Tribocharge (HH) (μC/g) | Tribocharge (LL) (μC/g) |
|---|---|---|---|---|---|---|
| 1A | SNOWTEX ZL | 16.5 | 0.81 | 0.76 | −24 | −50 |
| 1B | SNOWTEX OZL | 16.5 | 0.78 | 0.58 | −39 | −68 |

These results demonstrate that toner compositions comprising treated metal oxide particles that contain substantially no free alkali metal cations exhibit higher tribocharge than do toner compositions comprising treated metal oxide particles with a higher free alkali metal cation content.

Example 2

This example demonstrates the effect of the free alkali metal cation content of the treated metal oxide particles on the tribocharge of toner compositions comprising the treated metal oxide particles.

Three treated silica particle compositions (Compositions 2A-2C) were prepared as follows: 100 g of deionized water was added to 100 g of the silica dispersion indicated in Table 3 to reduce the concentration of silica to about 20 wt. %. In a separate beaker, 3.6 g OTES was dissolved in 90 mL of isopropyl alcohol (IPA) and then added to the silica dispersion with continuous agitation. The reaction mixture was continuously stirred and heated to 70-75° C. for 8 hours. Compositions 2A and 2B were then cooled to room temperature, poured into a glass dish, and dried in a forced-air oven at 120-130° C. Composition 2C was cooled to room temperature, and 10% acetic acid was then added to the reaction mixture to reduce the pH to about 6. The treated silica of Composition 2C was then separated by filtration, washed several times with an excess of deionized water, and dried in a forced-air oven at 120-130° C.

The carbon content of the dried particles before and after extraction with toluene is presented in Table 3. Extraction was a Soxhlet extraction using 0.5-2 g of silica and approximately 100 ml toluene.

Toner compositions were prepared using the treated particles in the manner previously described. The tribocharge values of the toner compositions are also provided in Table 3.

The total alkali metal cation content of the dried particles of Compositions 2A and 2C was determined by inductively-coupled plasma (ICP). The results are presented in Table 4. Table 4 also includes, for comparison, the total alkali metal cation content of the untreated commercially available silica dispersions (Compositions 2D-2E), which was also determined by ICP.

TABLE 3

| Composition | Silica | OTES (μmole/m$^2$) | Carbon Content (wt. %) | Carbon Content After Extraction (wt. %) | Tribocharge (HH) (μC/g) | Tribocharge (LL) (μC/g) |
|---|---|---|---|---|---|---|
| 2A | SNOWTEX ZL | 10.9 | 2.87 | 2.25 | −32 | −59 |
| 2B | SNOWTEX OZL | 10.9 | 5.09 | 4.27 | −39 | −81 |
| 2C | SNOWTEX ZL | 10.9 | 2.4 | 1.3 | −41 | −67 |

TABLE 4

| Sample | Dispersion | Treatment | Total alkali metal cation content in dry silica (wt. % Na) |
|---|---|---|---|
| 2A | SNOWTEX ZL | OTES | 0.45 |
| 2C | SNOWTEX ZL | OTES, also neutralized to pH 6 and washed | 0.35 |
| 2D | SNOWTEX ZL | None | 0.42 |
| 2E | SNOWTEX OZL | None | 0.31 |

The difference between the total alkali metal cation content before and after washing or ion-exchange represents the free alkali metal cation content. These results demonstrate that toner compositions comprising treated metal oxide particles that contain substantially no free alkali metal cations exhibit higher tribocharge than do toner compositions comprising treated metal oxide particles with a higher free alkali metal cation content (compare, for example, Composition 2A to Composition 2B). These results further demonstrate that the free alkali metal cation content of metal oxide particles is reduced by neutralization and washing of the metal oxide particles (compare, for example, Composition 2A to Composition 2C).

Example 3

This example demonstrates the treatment of metal oxide particles with a first hydrophobicity-imparting agent and a second hydrophobicity-imparting agent.

Three treated silica compositions (Compositions 3A-3C) were prepared as follows: 100 g of deionized water was added to 100 g of the silica dispersion indicated in Table 5 to reduce the concentration of silica to about 20 wt. %.

Compositions 3A and 3B were treated as follows: 3.2 g HMDZ was added to the dispersion, and the reaction mixture was stirred rapidly at 50-55° C. at a rate such that the vortex of the dispersion extended at least to the top of the agitator blade. The mixture was allowed to react for 5 hours. In a separate beaker, 2.2 g OTES was dissolved in 90 mL of isopropyl alcohol (IPA) and then added to the reaction mixture with continuous agitation. The temperature of the reaction mixture was raised to 70-75° C. and the mixture was allowed to react for 5 hours. The reaction mixture was cooled to room temperature, poured into a glass dish, and dried in a forced-air oven at 120-130° C. Composition 3C was prepared in the same manner as described above with respect to Compositions 3A-3B, except that Composition 3C was first treated with OTES at 70-75° C. for 5 hours, and then cooled and treated with HMDZ at 50-55° C. for an additional 5 hours.

The carbon content of the dried particles before and after extraction with toluene is presented in Table 5. Extraction was a Soxhlet extraction using 0.5-2 g of silica and approximately 100 ml toluene.

Toner compositions were prepared using the treated particles in the manner previously described. The tribocharge values of the toner compositions are provided in Table 6.

TABLE 5

| Composition | Silica | HMDZ (μmole/m$^2$) | OTES (μmole/m$^2$) | Carbon Content (wt. %) | Carbon Content After Extraction (wt. %) |
|---|---|---|---|---|---|
| 3A | SNOWTEX ZL | 16.6 | 6.6 | 1.9 | 1.4 |
| 3B | SNOWTEX OZL | 16.6 | 6.6 | 3.41 | 1.66 |
| 3C | SNOWTEX OZL | 16.6 | 6.6 | 1.81 | 0.93 |

TABLE 6

| Composition | Tribocharge (HH) (μC/g) | Tribocharge (LL) (μC/g) |
|---|---|---|
| 3A | −31 | −54 |
| 3B | −40 | −69 |
| 3C | −37 | −70 |

These results demonstrate that toner compositions comprising treated metal oxide particles that contain substantially no free alkali metal cations exhibit higher tribocharge than do toner compositions comprising treated metal oxide particles with a higher free alkali metal cation content (compare, for example, Composition 3A to Composition 3B). These results further demonstrate that toner compositions comprising metal oxide particles treated with both a first and a second hydrophobicity-agent exhibit similar tribocharge to toner compositions comprising similarly treated metal oxide particles, regardless of the order of treatment.

Example 4

This example demonstrates the procedure for determining the free alkali metal cation content of metal oxide particles according to the invention.

An Ion Selective Electrode (ISE) was used to determine the free alkali metal content in treated and untreated silica compositions. Specifically, an Accument Na ISE (model #13-620-503) and an Oakton Ion 6 combination meter were used to measure the potential of treated and untreated silica compositions. Using standard solutions of known sodium concentration and of fixed ionic strength, a calibration curve was generated to relate the measured potential (mV) to the sodium concentration. The calibration curve is represented by the following equation: mV=a*(ln [Na])−b, wherein the constants a and b are determined from the calibration curve. The calibration curve generated for this example had the following constant values: a=22.524 and b=172.59.

The free alkali metal cation content of two untreated silica particle compositions (Compositions 4A-4B) was determined by directly measuring the potential of the aqueous colloidal dispersion according to the ISE procedure described above.

Two treated silica particle compositions (Compositions 4C-4D) were prepared as follows: 100 g of deionized water was added to 100 g of the silica dispersion indicated in Table 7 to reduce the concentration of silica to about 20 wt. %. In a separate beaker, 3.6 g OTES was dissolved in 90 mL of IPA and then added to the silica dispersion with continuous agitation. The reaction mixture was continuously stirred and heated to 70-75° C. for 8 hours. The reaction mixture was cooled to room temperature, poured into a glass dish, and dried in a forced-air oven at 120-130° C.

The dried treated silica compositions were formulated into a water/alcohol slurry to facilitate the measurement of the free alkali metal content. The slurry of the dried treated silica compositions was prepared as follows: 12.2 g of deionized water, 1.7 g isopropyl alcohol (IPA), and 1.1 g of an ionic strength adjustor (ISA) were added to 0.42 g of the treated silica particle composition to formulate a slurry. The ionic strength adjustor (ISA) was added to the slurry in an amount of approximately 10 wt. % to keep the ionic strength of the composition high, thereby reducing variation in the measured potentials. The ISA is an aqueous solution consisting of 4M ammonium chloride and 4M ammonium hydroxide. The free alkali metal content of the treated silica compositions was determined according to the ISE procedure described above. The free alkali metal content of the silica compositions is presented in Table 7.

TABLE 7

| Sample | Dispersion | Treatment | Free alkali metal content (wt. % Na) |
|---|---|---|---|
| 4A | SNOWTEX YL | None | 0.31 |
| 4B | SNOWTEX OYL | None | 0.06 |
| 4C | SNOWTEX YL | OTES | 0.31 |
| 4D | SNOWTEX OYL | OTES | 0.11 |

Example 5

This example demonstrates the preparation of hydrophobic metal oxide particles by treating colloidal silica particles with a first hydrophobicity-imparting agent and a second hydrophobicity-imparting agent.

A reaction vessel was charged with 39 kg of SNOWTEX OYL colloidal silica dispersion. While continually agitating the dispersion with a stirrer and recirculating through a homogenizer, 25 kg of deionized water was added to the dispersion to reduce the concentration of colloidal silica to approximately 12 wt. %. 2.51 kg of HMDZ was then added to the dispersion, with continued agitation and recirculation. The reaction mixture was heated to 53° C. and allowed to react for 3 hours. At that time, approximately 26 L of the dispersion was transferred to the spray drier and dried.

24.6 kg isopropyl alcohol (IPA) (IPA/water volume ratio approximately 0.7) was added to the remaining volume of the dispersion in the reactor. 0.61 kg of OTES was added to the dispersion, and the reaction mixture was heated to approximately 70° C., and allowed to react for approximately 5.5 hours with continued stirring and recirculation.

The heat input to the reactor was stopped, but stirring and recirculation continued overnight. The slurry was spray dried the following day at a temperature of approximately 125° C. (dryer exit temperature). The inlet temperature to the dryer was 235° C. The powder was collected from both the cyclone collector and the bag filter. After drying, the powder was jet milled.

The resulting particle composition had a carbon content of 2.12 wt. %, and a surface area of 27.9 $m^2/g$. The tap density of the particle composition was determined after various numbers of taps, and the results were as follows: 228 g/L (0 taps), 297 g/L (300 taps), 304 g/L (600 taps), 308 g/L (1250 taps), and 312 g/L (3000 taps).

A toner composition was prepared using the particle composition in the manner previously described. The resulting toner composition had a tribocharge (HH) of −36 μC/g, and a tribocharge (LL) of −71 μC/g.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preparing hydrophobic metal oxide particles comprising
   (a) providing an aqueous dispersion of non-aggregated metal oxide particles, wherein the aqueous dispersion is basic,
   (b) combining the dispersion with a first hydrophobicity-imparting agent to provide a reaction mixture, wherein the first hydrophobicity-imparting agent is an alkoxysilane compound selected from the group consisting of monoalkoxysilane compounds, dialkoxysilane compounds, and trialkoxysilane compounds,
   (c) maintaining the reaction mixture at a temperature of about 40° C. to about 100° C., and
   (d) drying the reaction mixture to provide hydrophobic, non-aggregated, metal oxide particles in the form of a dry powder, wherein the hydrophobic metal oxide particles contain substantially no free alkali metal cations, and wherein a carbon content of the hydrophobic metal oxide particles is from about 3 wt % to about 8 wt % and a solid-state Si nuclear magnetic resonance spectrum of the hydrophobic metal oxide particles exhibits a ratio T3:T2 of about 0.4 to about 10, wherein T2 is the intensity of a peak having a chemical shift in the CP/MAS$^{29}$Si NMR spectrum centered within the range of 56 ppm to 59 ppm, and wherein T3 is the intensity of a peak having a chemical shift in the CP/MAS$^{29}$Si NMR spectrum centered within the range of −65 ppm to −69 ppm.

2. The method of claim 1, wherein the first hydrophobicity-imparting agent is a trialkoxysilane compound.

3. The method of claim 2, wherein the trialkoxysilane compound is octyltriethoxysilane.

4. The method of claim 1, wherein part (b) further comprises combining the dispersion with a second hydrophobicity-imparting agent.

5. The method of claim 4, wherein the second hydrophobicity-imparting agent is an aza-silane.

6. The method of claim 4, wherein the second hydrophobicity-imparting agent is an aminoalkylsilane.

7. The method of claim 4, wherein the second hydrophobicity-imparting agent is hexamethyldisilazane.

8. The method of claim 1, wherein an agglomerate particle size of the hydrophobic metal oxide particles is reduced after the dispersion is dried.

9. The method of claim 1, wherein the dispersion is prepared by mixing an aqueous metal oxide dispersion with a water-miscible organic solvent, before contacting the metal oxide particles with the first hydrophobicity-imparting agent.

10. The method of claim 4, wherein the dispersion is prepared by mixing an aqueous metal oxide dispersion with a water-miscible organic solvent, before contacting the metal oxide particles with the second hydrophobicity-imparting agent.

11. The method of claim 10, wherein the organic solvent to water volume ratio is between about 0.2 and about 2.

12. The method of claim 1, wherein the reaction mixture is maintained at a temperature between about 40° C. and about 80° C. for about 1 hour or longer.

13. The method of claim 1, wherein the dispersion comprises between about 10 wt. % and about 45 wt. % metal oxide particles.

14. The method of claim 1, wherein the metal oxide particles are colloidal silica particles.

15. The method of claim 14, wherein the colloidal silica particles are prepared from an alkali silicate.

16. The method of claim 1, wherein the aqueous dispersion has a pH of about 8 to about 11.

* * * * *

UNITED STATES PATENT AND TRADEMARK OFFICE
CERTIFICATE OF CORRECTION

PATENT NO. : 10,407,571 B2  
APPLICATION NO. : 15/454089  
DATED : September 10, 2019  
INVENTOR(S) : Dmitry Fomitchev et al.

Page 1 of 1

It is certified that error appears in the above-identified patent and that said Letters Patent is hereby corrected as shown below:

In the Claims

At Column 20, Line 30, corresponding to Claim 1, that portion of the sentence reading "56 ppm" should read -- -56 ppm -- and;

At Column 20, Line 30, corresponding to Claim 1, that portion of the sentence reading "59 ppm" should read -- -59 ppm --.

Signed and Sealed this  
Twenty-fifth Day of February, 2020

Andrei Iancu  
*Director of the United States Patent and Trademark Office*